United States Patent
Makled et al.

(10) Patent No.: US 9,874,549 B2
(45) Date of Patent: Jan. 23, 2018

(54) METHODS AND SYSTEMS FOR OPERATING A VARIABLE VOLTAGE OXYGEN SENSOR

(71) Applicant: Ford Global Technologies, LLC, Dearborn, MI (US)

(72) Inventors: Daniel A. Makled, Dearborn, MI (US); Gopichandra Surnilla, West Bloomfield, MI (US); Richard E. Soltis, Saline, MI (US); Susan Nicole Wilber, Livonia, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 298 days.

(21) Appl. No.: 14/517,601

(22) Filed: Oct. 17, 2014

(65) Prior Publication Data
US 2016/0109422 A1 Apr. 21, 2016

(51) Int. Cl.
| | | |
|---|---|---|
| *G01R 31/00* | (2006.01) | |
| *G01N 33/00* | (2006.01) | |
| *F02D 41/12* | (2006.01) | |
| *F02D 41/20* | (2006.01) | |
| *F02D 19/06* | (2006.01) | |
| *F02D 13/02* | (2006.01) | |
| *F02D 41/14* | (2006.01) | |

(52) U.S. Cl.
CPC ..... *G01N 33/0073* (2013.01); *F02D 13/0203* (2013.01); *F02D 19/0655* (2013.01); *F02D 41/123* (2013.01); *F02D 41/1454* (2013.01); *F02D 41/20* (2013.01); *F02D 2041/1472* (2013.01); *F02D 2041/2051* (2013.01); *F02D 2200/0418* (2013.01); *F02D 2200/0612* (2013.01); *Y02T 10/18* (2013.01); *Y02T 10/36* (2013.01)

(58) Field of Classification Search
CPC ...... G01R 15/246; G01R 15/242; G01R 1/71; G01R 1/203
USPC ....... 324/96, 76, 76.11, 114.01, 114.81, 169, 324/73, 378, 503
See application file for complete search history.

(56) References Cited

U.S. PATENT DOCUMENTS

| | | | | |
|---|---|---|---|---|
| 4,401,086 A | * | 8/1983 | Miyagi | ............... F02D 41/1474 123/696 |
| 4,596,217 A | * | 6/1986 | Bonitz | .................. F02P 5/1521 123/406.36 |
| 4,614,175 A | * | 9/1986 | Asayama | ............ F02D 41/0052 123/568.26 |

(Continued)

OTHER PUBLICATIONS

Surnilla, Gopichandra et al., "Method for Estimating Charge Air Cooler Condensation Storage and/or Release with an Intake Oxygen Sensor," U.S. Appl. No. 13/967,968, filed Aug. 15, 2013, 57 pages.

(Continued)

*Primary Examiner* — Tung X Nguyen
*Assistant Examiner* — Dominic Hawkins
(74) *Attorney, Agent, or Firm* — Julia Voutyras; McCoy Russell LLP (57) ABSTRACT

Methods and systems are provided for adjusting a rate of change in a reference voltage of an oxygen sensor. In one example, a method may include gradually increasing a reference voltage of an oxygen sensor from a lower first voltage to a higher second voltage at a ramp rate. The ramp rate may be based on engine operating conditions.

20 Claims, 7 Drawing Sheets

(56) References Cited

U.S. PATENT DOCUMENTS

| | | | | |
|---|---|---|---|---|
| 4,741,318 | A | * | 5/1988 | Kortge ................ F02D 41/0042 123/520 |
| 5,056,308 | A | * | 10/1991 | Kume ................ F02D 41/1443 123/443 |
| 5,121,732 | A | * | 6/1992 | Benninger .......... F02D 19/0628 123/434 |
| 5,145,566 | A | | 9/1992 | Logothetis et al. |
| 5,363,831 | A | * | 11/1994 | Tomisawa ........... F02D 41/1477 123/695 |
| 5,833,836 | A | * | 11/1998 | Takami ............... F02D 41/1496 204/424 |
| 6,354,077 | B1 | * | 3/2002 | Behr ................... F02D 41/0082 60/274 |
| 6,591,605 | B2 | * | 7/2003 | Lewis ................ F02D 41/1441 60/274 |
| 8,522,760 | B2 | | 9/2013 | Soltis |
| 8,763,594 | B2 | | 7/2014 | Surnilla et al. |
| 8,857,155 | B2 | | 10/2014 | Surnilla et al. |
| 9,354,213 | B2 | * | 5/2016 | Fey .................... G01N 33/0006 |
| 2009/0192694 | A1 | * | 7/2009 | Mullen ............... F02D 41/1454 701/103 |
| 2010/0070159 | A1 | * | 3/2010 | Iwahashi ................ F02D 13/02 701/105 |
| 2010/0229837 | A1 | * | 9/2010 | Peters ................. F02D 41/0032 123/520 |
| 2011/0132342 | A1 | * | 6/2011 | Soltis ................. F02D 41/0025 123/703 |
| 2012/0037134 | A1 | | 2/2012 | Jankovic et al. |
| 2014/0012486 | A1 | * | 1/2014 | Fey ........................ F02D 41/00 701/103 |
| 2014/0202426 | A1 | | 7/2014 | Surnilla et al. |
| 2014/0202437 | A1 | | 7/2014 | Surnilla et al. |
| 2014/0253072 | A1 | * | 9/2014 | Hussien .................. H02M 1/36 323/281 |
| 2014/0373822 | A1 | * | 12/2014 | Rosswurm .......... F02D 41/0027 123/676 |
| 2015/0047339 | A1 | * | 2/2015 | Rollinger ............ F02B 29/0468 60/599 |
| 2015/0135802 | A1 | * | 5/2015 | Fey .................... F02D 41/1454 73/23.21 |

OTHER PUBLICATIONS

Rollinger, John E. et al., "Method for Estimating Charge Air Cooler Condensation Storage and/or Release with Two Intake Oxygen Sensors," U.S. Appl. No. 13/967,943, filed Aug. 15, 2013, 58 pages.

Surnilla, Gopichandra et al., "Methods and Systems for Indicating Water at an Oxygen Sensor Based on Sensor Heater Power Consumption," U.S. Appl. No. 13/971,714, filed Aug. 20, 2013, 32 pages.

Surnilla, Gopichandra et al., "Methods and Systems for an Intake Oxygen Sensor," U.S. Appl. No. 14/032,103, filed Sep. 19, 2013, 43 pages.

Surnilla, Gopichandra et al., "Methods and Systems for an Intake Oxygen Sensor," U.S. Appl. No. 14/032,109, filed Sep. 19, 2013, 44 pages.

Surnilla, Gopichandra et al., "Methods and Systems for Adjusting Engine Airflow Based on Output from an Oxygen Sensor," U.S. Appl. No. 14/063,896, filed Oct. 25, 2013, 36 pages.

Surnilla, Gopichandra et al., "Methods for Estimating Charge Air Cooler Condensation Storage with an Intake Oxygen Sensor," U.S. Appl. No. 14/065,147, filed Oct. 28, 2013, 39 pages.

Surnilla, Gopichandra et al., "Methods and Systems for PCV Flow Estimation with an Intake Oxygen Sensor," U.S. Appl. No. 14/073,480, filed Nov. 6, 2013, 52 pages.

Surnilla, Gopichandra et al., "Methods and Systems for Fuel Ethanol Content Determination via an Oxygen Sensor," U.S. Appl. No. 14/151,574, filed Jan. 9, 2014, 31 pages.

Vigild, Christian W. et al., "Methods and Systems for Fuel Canister Purge Flow Estimation with an Intake Oxygen Sensor," U.S. Appl. No. 14/155,261, filed Jan. 14, 2014, 51 pages.

Surnilla, Gopichandra et al., "Methods and Systems for Fuel Ethanol Content Determination via an Oxygen Sensor," U.S. Appl. No. 14/297,301, filed Jun. 5, 2014, 35 pages.

Surnilla, Gopichandra et al., "Methods and Systems for Adjusting Heater Power of an Oxygen Sensor to Reduce Degradation from Water," U.S. Appl. No. 14/326,385, filed Jul. 8, 2014, 38 pages.

* cited by examiner

METHODS AND SYSTEMS FOR OPERATING A VARIABLE VOLTAGE OXYGEN SENSOR

FIELD

The present description relates generally to methods and systems for adjusting operation of a variable voltage oxygen sensor of an internal combustion engine to reduce degradation of the sensor.

BACKGROUND/SUMMARY

Intake and/or exhaust gas sensors may be operated to provide indications of various exhaust gas constituents. For example, US 20120037134 describes detecting engine intake dilution using an intake gas oxygen sensor. In alternate approaches, engine dilution may be estimated by an exhaust gas oxygen sensor. The estimated engine dilution may be used to adjust various engine operating parameters, such as fueling and air-fuel ratio. As another example, U.S. Pat. No. 5,145,566 describes detecting water content in the exhaust gas using an exhaust gas oxygen sensor. Water content estimated using an intake or exhaust gas oxygen sensor may be used to infer an ambient humidity during engine operation and/or an alcohol content of a fuel burned in the engine.

In some examples, the oxygen sensor may be a variable voltage (VVs) oxygen sensor. A reference voltage of the VVs oxygen sensor may be adjustable between a lower base voltage where water is not dissociated and a higher target voltage where water is dissociated. The outputs of the oxygen sensor at the two reference voltages may then be used to determine water content of the intake or exhaust air of the engine.

However, the inventors herein have recognized potential issues with repeatedly changing the VVs oxygen sensor reference voltage directly from the base voltage to the target voltage and back again. As one example, repeated transitions between reference voltages may result in sensor blackening and/or pumping current ringing. For example, single step transitions between a lower and higher reference voltage may result in large overshoots in both pumping cell voltage and pumping current of the VVs sensor. This may cause sensor degradation when repeated over thousands of cycles. Long settling times caused by ringing may degrade the ability for the oxygen sensor to return to its base reference voltage, thereby increasing a time spent in open loop fuel operation.

In one example, the issues described above may be addressed by a method for increasing a reference voltage of an oxygen sensor from a first voltage to a second voltage gradually at a ramp rate, the ramp rate based on engine operating conditions. In this way, the reference voltage of the oxygen sensor may be changed more gradually, thereby reducing stress on the sensor and improving the longevity of the sensor.

As one example, increasing the reference voltage of the oxygen sensor from the first voltage to the second voltage may include transitioning from the first to the second voltage incrementally in a series of steps at the ramp rate instead of in a single step. The ramp rate may be based on engine operating conditions such as ambient humidity and engine fueling. For example, sensor overshoot, undershoot, and settling may increase under low humidity conditions and/or when mostly ambient air is flowing across the sensor (such as during a deceleration fuel shut-off event). Thus, by decreasing the ramp rate during low humidity and/or decreased engine fueling conditions, sensor blackening and ringing due to overshoot, undershoot, and settling times may be reduced, thereby reducing degradation of the oxygen sensor.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
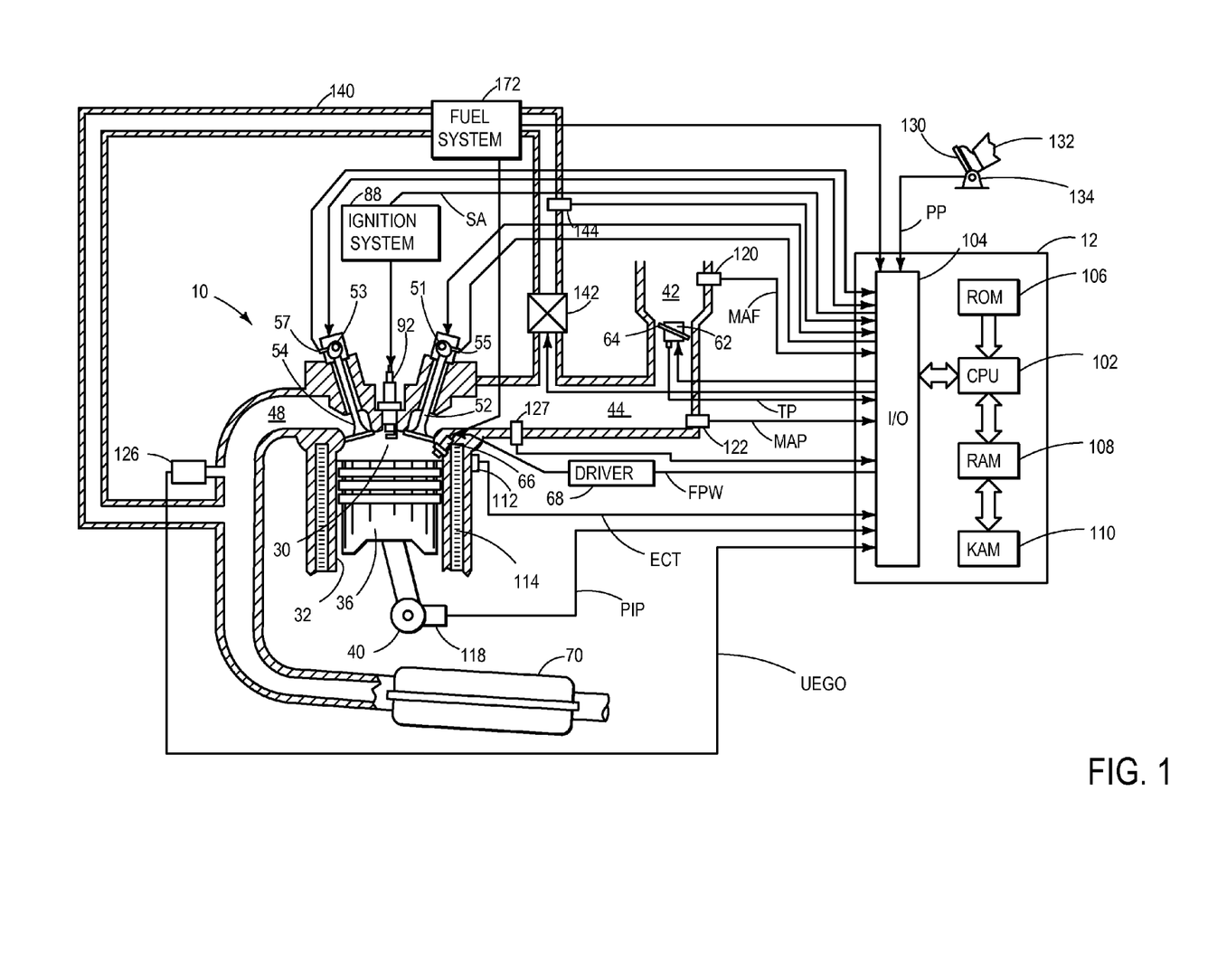
FIG. 1 shows a schematic diagram of an engine including an exhaust gas oxygen sensor and an intake gas oxygen sensor.
Figure 2:
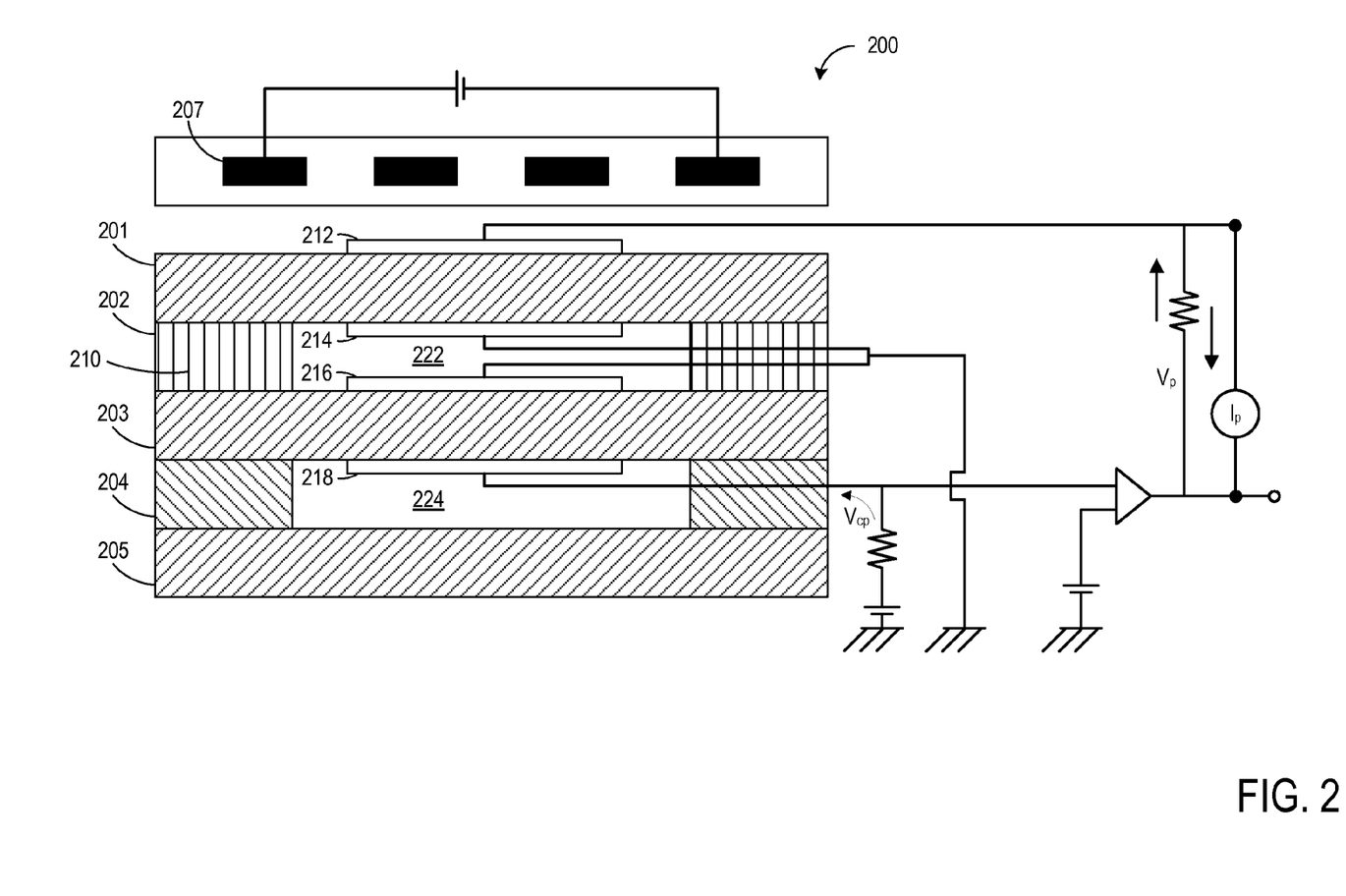
FIG. 2 shows a schematic diagram of an example oxygen sensor.
Figure 3:
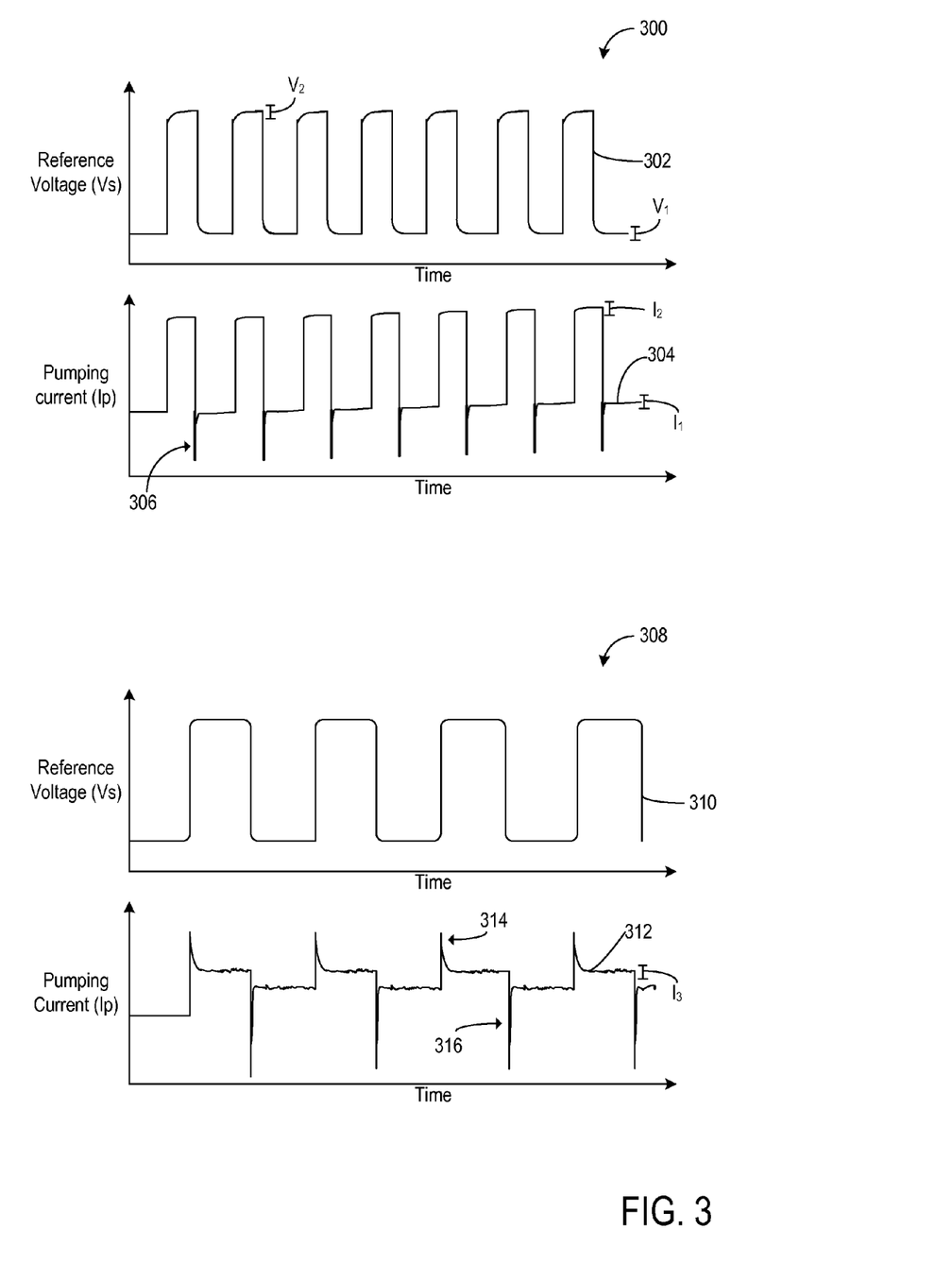
FIG. 3 shows two graphs of example changes in a reference voltage (Vs) of an oxygen sensor using a single step change and the resulting pumping current (Ip) during different vehicle fueling conditions.
Figure 4:
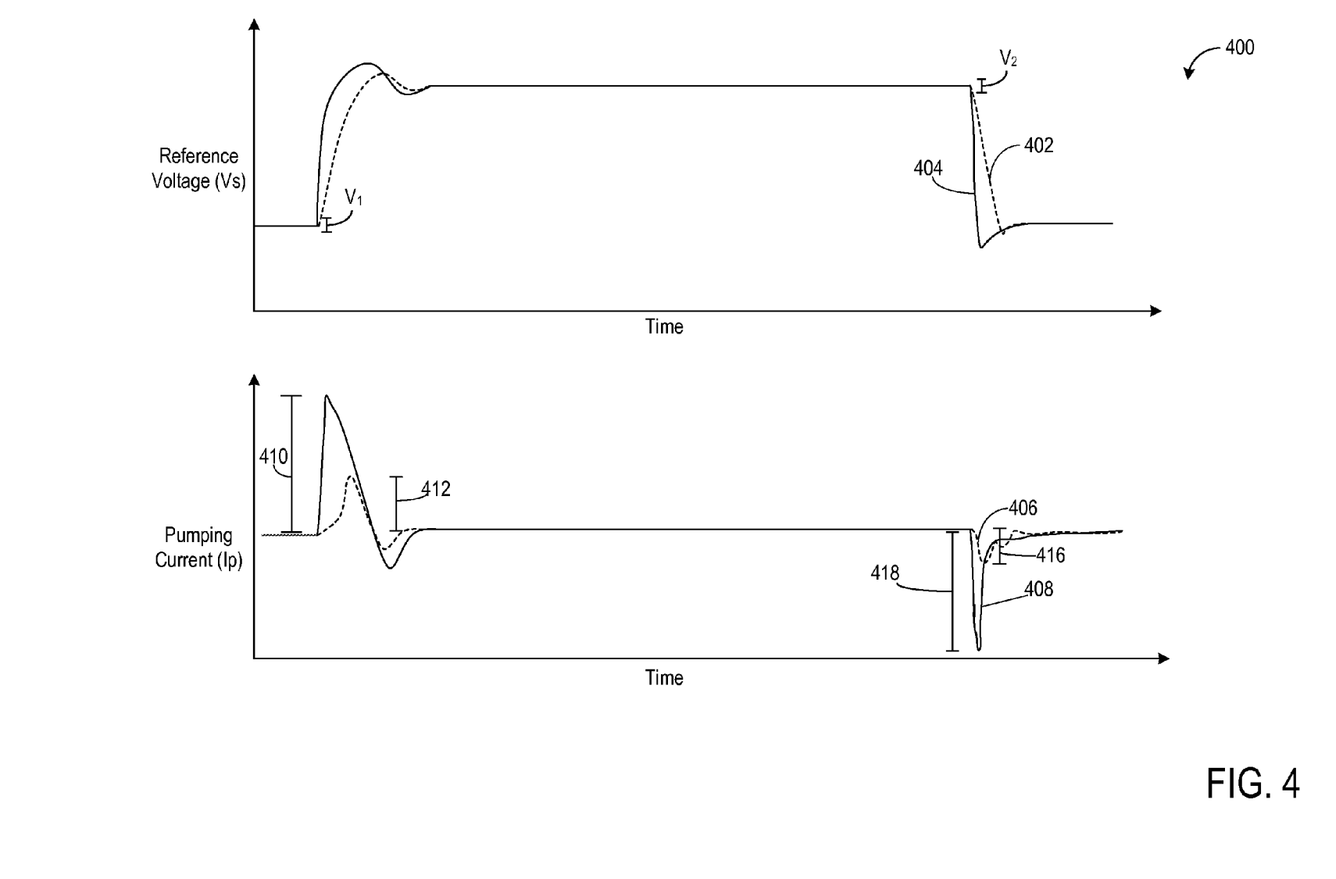
FIG. 4 shows a graph of example changes in pumping current of an oxygen sensor in response to changes in reference voltage of the oxygen sensor at different rates.
Figure 7:
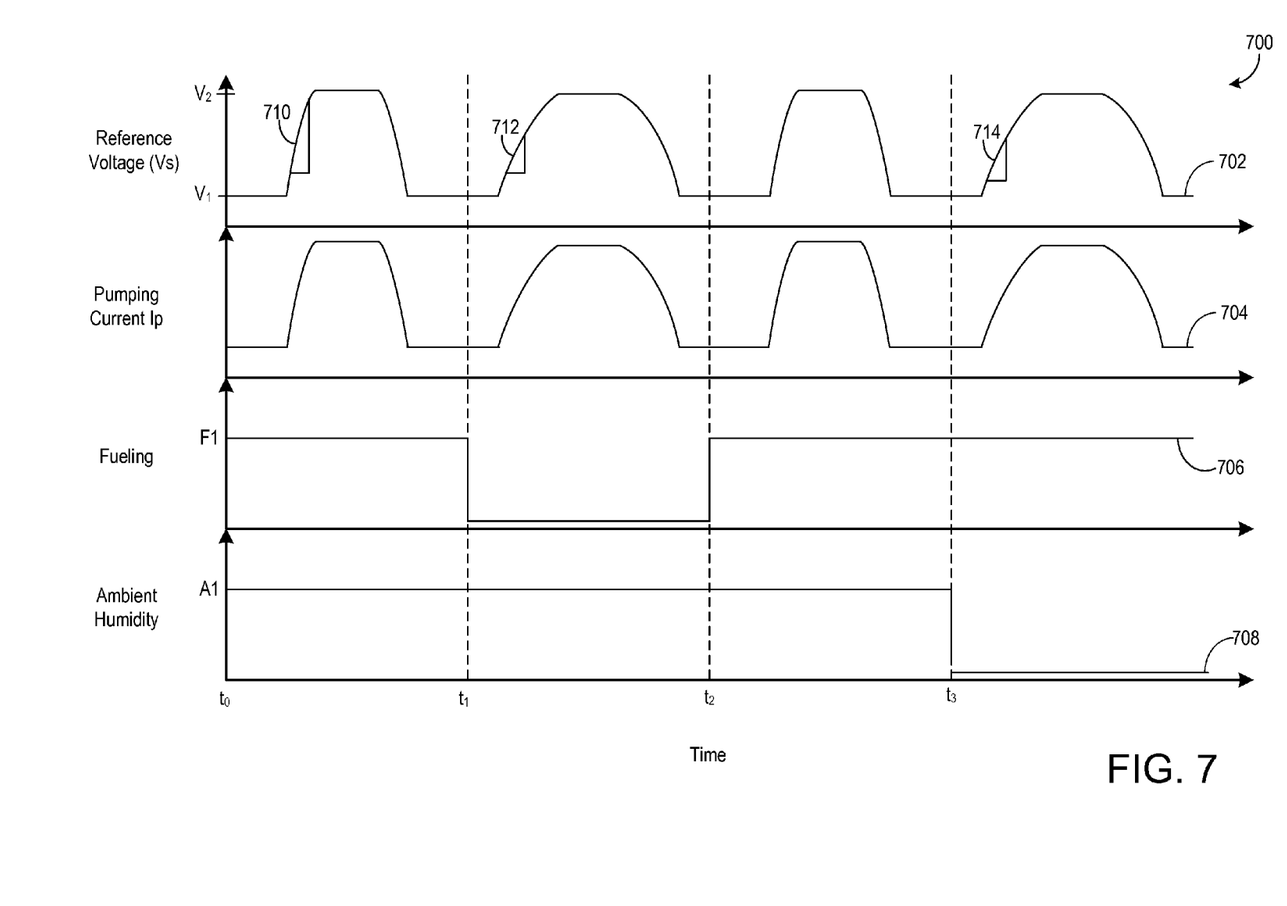
FIG. 7 shows a graph illustrating changes in a ramp rate of a reference voltage of an oxygen sensor based on engine operating parameters.

The following detailed description relates to systems and methods for adjusting a rate of change in a reference voltage of an oxygen sensor. A vehicle engine, as shown in FIG. 1, may include an oxygen sensor located in an intake and/or exhaust passage of the engine. The oxygen sensor may be a variable voltage (VVs) oxygen sensor, as depicted in FIG. 2, where a reference voltage of the VVs oxygen sensor is adjustable between a lower base reference voltage and a higher reference voltage. In one example, transitioning between a lower and higher reference voltage values in one step may result in overshoots and/or undershoots in both pumping cell voltage and pumping current of the VVs oxygen sensor, as seen in FIG. 3. This may cause oxygen sensor degradation when repeated over multiple consecutive cycles. As one example, oxygen sensor degradation may be reduced by gradually increasing the reference voltage of the oxygen sensor (e.g., ramping) from a lower, first reference voltage to a higher, second reference voltage at a gradual rate or in incremental steps. In this way, the overshoots and undershoots in pumping cell voltage and pumping current may be reduced, as depicted in FIG. 4. Example methods for gradually changing the reference voltage of an oxygen sensor to reduce degradation are described in FIG. 5. For example, a method may include increasing the reference voltage of the oxygen sensor from a lower first voltage to an intermediate voltage with a single step change and then increasing from the intermediate voltage to a higher second voltage at a reduced rate, the intermediate voltage between the first and second voltages. The rate of change in the reference voltage may also be adjusted based on engine operating parameters such as engine fueling and/or ambient humidity, as shown in FIG. 7. In this way, stress on an oxygen sensor may be decreased and longevity of the oxygen sensor may be increased, thereby increasing engine control based on an output of the oxygen sensor.

Referring now to FIG. 1, a schematic diagram showing one cylinder of a multi-cylinder engine 10, which may be included in a propulsion system of an automobile, is illustrated. The engine 10 may be controlled at least partially by a control system including a controller 12 and by input from a vehicle operator 132 via an input device 130. In this example, the input device 130 includes an accelerator pedal and a pedal position sensor 134 for generating a proportional pedal position signal PP. A combustion chamber (i.e., cylinder) 30 of the engine 10 may include combustion chamber walls 32 with a piston 36 positioned therein. The piston 36 may be coupled to a crankshaft 40 so that reciprocating motion of the piston is translated into rotational motion of the crankshaft. The crankshaft 40 may be coupled to at least one drive wheel of a vehicle via an intermediate transmission system. Further, a starter motor may be coupled to the crankshaft 40 via a flywheel to enable a starting operation of the engine 10.

The combustion chamber 30 may receive intake air from an intake manifold 44 via an intake passage 42 and may exhaust combustion gases via an exhaust passage 48. The intake manifold 44 and exhaust passage 48 can selectively communicate with the combustion chamber 30 via respective intake valve 52 and exhaust valve 54. In some embodiments, the combustion chamber 30 may include two or more intake valves and/or two or more exhaust valves.

In this example, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by a controller 12 to vary valve operation. The position of the intake valve 52 and exhaust valve 54 may be determined by position sensors 55 and 57, respectively. In alternative embodiments, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

In some embodiments, each cylinder of the engine 10 may be configured with one or more fuel injectors for providing fuel thereto. As a non-limiting example, the cylinder 30 is shown including one fuel injector 66. The fuel injector 66 is shown coupled directly to the cylinder 30 for injecting fuel directly therein in proportion to the pulse width of signal FPW received from the controller 12 via an electronic driver 68. In this manner, the fuel injector 66 provides what is known as direct injection (hereafter also referred to as "DI") of fuel into the combustion cylinder 30.

It will be appreciated that in an alternate embodiment, the injector 66 may be a port injector providing fuel into the intake port upstream of the cylinder 30. It will also be appreciated that the cylinder 30 may receive fuel from a plurality of injectors, such as a plurality of port injectors, a plurality of direct injectors, or a combination thereof.

A fuel tank in a fuel system 172 may hold fuels with different fuel qualities, such as different fuel compositions. These differences may include different alcohol content, different octane, different heats of vaporization, different fuel blends, and/or combinations thereof etc. The engine may use an alcohol containing fuel blend such as E85 (which is approximately 85% ethanol and 15% gasoline) or M85 (which is approximately 85% methanol and 15% gasoline). Alternatively, the engine may operate with other ratios of gasoline and ethanol stored in the tank, including 100% gasoline and 100% ethanol, and variable ratios therebetween, depending on the alcohol content of fuel supplied by the operator to the tank. Moreover, fuel characteristics of the fuel tank may vary frequently. In one example, a driver may refill the fuel tank with E85 one day, and E10 the next, and E50 the next. As such, based on the level and composition of the fuel remaining in the tank at the time of refilling, the fuel tank composition may change dynamically.

The day to day variations in tank refilling can thus result in frequently varying fuel composition of the fuel in the fuel system 172, thereby affecting the fuel composition and/or fuel quality delivered by the injector 66. The different fuel compositions injected by the injector 66 may herein be referred to as a fuel type. In one example, the different fuel compositions may be qualitatively described by their research octane number (RON) rating, alcohol percentage, ethanol percentage, etc.

It will be appreciated that while in one embodiment, the engine may be operated by injecting the variable fuel blend via a direct injector, in alternate embodiments, the engine may be operated by using two injectors and varying a relative amount of injection from each injector. It will be further appreciated that when operating the engine with a boost from a boosting device such as a turbocharger or supercharger (not shown), the boosting limit may be increased as an alcohol content of the variable fuel blend is increased.

Continuing with FIG. 1, the intake passage 42 may include a throttle 62 having a throttle plate 64. In this particular example, the position of the throttle plate 64 may be varied by the controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle plate 64 may be provided to the controller 12 by a throttle position signal TP. The intake passage 42 may include a mass air flow sensor 120 and a manifold air pressure sensor 122 for providing respective signals MAF and MAP to controller 12.

An ignition system 88 can provide an ignition spark to the combustion chamber 30 via a spark plug 92 in response to a spark advance signal SA from the controller 12, under select operating modes. Though spark ignition components are shown, in some embodiments, the combustion chamber 30 or one or more other combustion chambers of the engine 10 may be operated in a compression ignition mode, with or without an ignition spark.

A variable voltage (VVs) oxygen sensor 126, is shown coupled to the exhaust passage 48 upstream of an emission control device 70. The emission control device 70 is shown arranged along the exhaust passage 48 downstream of the VVs oxygen sensor 126. The device 70 may be a three way catalyst (TWC), $NO_x$ trap, various other emission control devices, or combinations thereof. In some embodiments, during operation of engine 10, emission control device 70 may be periodically reset by operating at least one cylinder of the engine within a particular air/fuel ratio.

As shown in the example of FIG. 1, the system further includes an intake air sensor 127 coupled to the intake passage 44. The sensor 127 may be a VVs oxygen sensor, but it may also be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor.

Further, in the disclosed embodiments, an exhaust gas recirculation (EGR) system may route a desired portion of exhaust gas from the exhaust passage 48 to the intake passage 44 via an EGR passage 140. The amount of EGR provided to the intake passage 44 may be varied by the controller 12 via an EGR valve 142. Further, an EGR sensor 144 may be arranged within the EGR passage 140 and may provide an indication of one or more of pressure, temperature, and concentration of the exhaust gas. Under some conditions, the EGR system may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

The controller 12 is shown in FIG. 1 as a microcomputer, including a microprocessor unit 102, input/output ports 104, an electronic storage medium for executable programs and calibration values shown as read only memory chip 106 in this particular example, random access memory 108, keep alive memory 110, and a data bus. The controller 12 may receive various signals from sensors coupled to the engine 10, in addition to those signals previously discussed, including measurement of inducted mass air flow (MAF) from the mass air flow sensor 120; engine coolant temperature (ECT) from a temperature sensor 112 coupled to a cooling sleeve 114; a profile ignition pickup signal (PIP) from a Hall effect sensor 118 (or other type) coupled to the crankshaft 40; throttle position (TP) from a throttle position sensor; and absolute manifold pressure signal, MAP, from the sensor 122. Engine speed signal, RPM, may be generated by the controller 12 from signal PIP.

The storage medium read-only memory 106 can be programmed with computer readable data representing instructions executable by the processor 102 for performing the methods described below as well as other variants that are anticipated but not specifically listed.

As described above, FIG. 1 shows only one cylinder of a multi-cylinder engine, and each cylinder may similarly include its own set of intake/exhaust valves, fuel injector, spark plug, etc.

Next, FIG. 2 shows a schematic view of an example embodiment of an oxygen sensor 200 configured to measure a concentration of oxygen ($O_2$) in an intake airflow in an intake passage or an exhaust gas stream in an exhaust passage. The sensor 200 may operate as VVs oxygen sensor 126 or 127 of FIG. 1, for example. The sensor 200 comprises a plurality of layers of one or more ceramic materials arranged in a stacked configuration. In the embodiment of FIG. 2, five ceramic layers are depicted as layers 201, 202, 203, 204, and 205. These layers include one or more layers of a solid electrolyte capable of conducting ionic oxygen. Examples of suitable solid electrolytes include, but are not limited to, zirconium oxide-based materials. Further, in some embodiments, a heater 207 may be disposed in thermal communication with the layers to increase the ionic conductivity of the layers. While the depicted oxygen sensor is formed from five ceramic layers, it will be appreciated that the oxygen sensor may include other suitable numbers of ceramic layers.

The layer 202 includes a material or materials creating a diffusion path 210. The diffusion path 210 is configured to introduce exhaust gases into a first internal cavity 222 via diffusion. The diffusion path 210 may be configured to allow one or more components of intake air or exhaust gases, including but not limited to a desired analyte (e.g., $O_2$), to diffuse into internal cavity 222 at a more limiting rate than the analyte can be pumped in or out by a pumping electrodes pair 212 and 214. In this manner, a stoichiometric level of $O_2$ may be obtained in the first internal cavity 222.

The sensor 200 further includes a second internal cavity 224 within the layer 204 separated from the first internal cavity 222 by the layer 203. The second internal cavity 224 is configured to maintain a constant oxygen partial pressure equivalent to a stoichiometric condition, e.g., an oxygen level present in the second internal cavity 224 is equal to that which the intake air or exhaust gas would have if the air-fuel ratio was stoichiometric. The oxygen concentration in the second internal cavity 224 is held constant by pumping voltage $V_{cp}$. Herein, the second internal cavity 224 may be referred to as a reference cell.

A pair of sensing electrodes 216 and 218 is disposed in communication with the first internal cavity 222 and the reference cell 224. The sensing electrodes pair 216 and 218 detects a concentration gradient that may develop between the first internal cavity 222 and the reference cell 224 due to an oxygen concentration in the intake air or exhaust gas that is higher than or lower than the stoichiometric level. A high oxygen concentration may be caused by a lean intake air or exhaust gas mixture, while a low oxygen concentration may be caused by a rich mixture.

A pair of pumping electrodes 212 and 214 is disposed in communication with the internal cavity 222, and is configured to electrochemically pump a selected gas constituent (e.g., $O_2$) from internal cavity 222 through layer 201 and out of the sensor 200. Alternatively, the pair of pumping electrodes 212 and 214 may be configured to electrochemically pump a selected gas through layer 201 and into internal cavity 222. Herein, the pumping electrodes pair 212 and 214 may be referred to as an $O_2$ pumping cell.

The electrodes 212, 214, 216, and 218 may be made of various suitable materials. In some embodiments, the electrodes 212, 214, 216, and 218 may be at least partially made of a material that catalyzes the dissociation of molecular oxygen. Examples of such materials include, but are not limited to, electrodes containing platinum and/or silver.

The process of electrochemically pumping oxygen out of or into the internal cavity 222 includes applying a voltage $V_p$ across the pumping electrode pair 212 and 214. The pumping voltage $V_p$ applied to the $O_2$ pumping cell pumps oxygen into or out of the first internal cavity 222 in order to maintain a stoichiometric level of oxygen in the cavity pumping cell. The resulting pumping current $I_p$ is proportional to the concentration of oxygen in the exhaust gas. A control system (not shown in FIG. 2) generates the pumping current signal $I_p$ as a function of the intensity of the applied pumping voltage $V_p$ required to maintain a stoichiometric level within the first internal cavity 222. Thus, a lean mixture will cause oxygen to be pumped out of the internal cavity 222 and a rich mixture will cause oxygen to be pumped into the internal cavity 222.

It should be appreciated that the oxygen sensor described herein is merely an example embodiment of an oxygen sensor, and that other embodiments of oxygen sensors may have additional and/or alternative features and/or designs.

In one example, the oxygen sensor 200 (and the oxygen sensors 126 and 127 shown in FIG. 1) may be a variable voltage (variable Vs or VVs) oxygen sensor where a reference voltage of the sensor may be modulated between a lower or base voltage at which oxygen is detected (and water is not dissociated) and a higher voltage at which water molecules in the gas flow may be dissociated. For example, during base operation, the oxygen sensor may operate at the base reference voltage. At the base reference voltage, when water hits the sensor, the heated element of the sensor may evaporate the water and measure it as a local vapor or diluent. The oxygen sensor may also operate in a second mode wherein the reference voltage is increased to a second reference voltage. The second reference voltage may be higher than the base reference voltage. When the intake oxygen sensor operates at the second reference voltage, the heated element of the sensor dissociates water in the air and subsequently measures the water concentration. Thus, the resulting pumping current of the sensor at the second reference voltage may be indicative of an amount of oxygen in the gas flow plus an amount of oxygen from dissociated water molecules. A change in pumping current between the first voltage and the second voltage may then be indicative of an amount of water in a gas flow in which the oxygen sensor is position.

In this way, the VVs oxygen sensor of FIG. 2 may be used to estimate the oxygen content of fresh air received in the intake manifold (if the sensor is positioned in an intake passage of the engine) or the oxygen content of exhaust gas exhausted from the engine (if the sensor is position in an exhaust passage downstream from an engine cylinder). The VVs oxygen sensor may also be used to estimate an amount of alcohol in the fuel burned in the engine and ambient humidity.

Turning to FIG. 3, two graphs 300 and 308 show a changing reference voltage and resulting pumping current over time for a variable voltage oxygen sensor (e.g. VVs oxygen sensor 126 or 127 shown in FIG. 1). Graph 300 consists of two plots 302 and 304 that show the reference voltage and pumping current, respectively, of an oxygen sensor (e.g. VVs oxygen sensor) with respect to time under typical exhaust conditions. Both the reference voltage and pumping current of the oxygen sensor change periodically between a lower first value and upper second values. The first reference voltage, $V_1$, may have a value such that oxygen is pumped from the cell, but low enough that oxygen compounds such as water are not dissociated at the sensor (e.g., in one example, $V_1$ may be approximately 450 mV). Application of the first reference voltage $V_1$ may generate an output of the sensor in the form of a first pumping current, $I_1$, that is indicative of the amount of oxygen in the sample gas. Once the amount of oxygen is determined, a second pumping voltage, $V_2$, may be applied to the oxygen pumping cell of the oxygen sensor. The second voltage $V_2$ may be greater than the first voltage $V_1$ applied to the sensor. In particular, the second voltage $V_2$ may have a value high enough to dissociate a desired oxygen compound. For example, the second voltage $V_2$ may be high enough to dissociate water molecules into hydrogen and oxygen (e.g., in one example, $V_2$ may be approximately 1.1 V). Application of the second voltage $V_2$ may generate a second pumping current, $I_2$, that is indicative of the amount of oxygen and water in the sample gas. It will be understood that the term "water" in the "amount of oxygen and water" as used herein refers to the amount of oxygen from the dissociated water molecules in the sample gas.

The ambient humidity (e.g., absolute humidity of the fresh air surrounding the vehicle) may be determined based on the first pumping current and the second pumping current during a non-fueling condition (e.g., DFSO event). In this case, the first pumping current may be subtracted from the second pumping current to obtain a value indicative of the amount of oxygen from dissociated water molecules (e.g., the amount of water) in the sample gas. This value may be proportional to the ambient humidity. Additionally, the amount of alcohol in the fuel, and thus the fuel type, may be identified during a normal fueling condition. A normal fueling condition may hereinafter refer to any condition in which fuel is being injected into the engine cylinders. In this case, the amount of water in the exhaust gas may be proportional to an amount of alcohol (e.g., a percent of ethanol) in the fuel injected to the engine. Because ambient humidity may also contribute to an amount of water in the exhaust gas, the ambient humidity determined during a non-fueling condition (e.g. DFSO event) may be subtracted from the amount of water to give a more accurate measurement of the amount of alcohol in the fuel injected to the engine.

Returning to graph 300, the reference voltage of the oxygen sensor transitions between the first voltage $V_1$ and the second voltage $V_2$ via a single step change. Said another way, the reference voltage changes directly from the first voltage $V_1$ to the second voltage $V_2$ and back again without transitioning to any intermediate voltages between the first voltage $V_1$ and the second voltage $V_2$. Correspondingly, the pumping current also transitions from the first pumping current $I_1$ and the second pumping current $I_2$ and back again. However, as shown in graph 300, the pumping current undershoots its lower value ($I_1$) as a result of the reference voltage change occurring in one single step from its upper to lower value. The Ip undershoot 306 can lead to sensor degradation if it persists for multiple repeated cycles (e.g., thousands of cycles).

Graph 308 consists of two plots 310 and 312 that show the reference voltage and pumping current, respectively, of the oxygen sensor over time under engine non-fueling conditions. In one example, the non-fueling conditions may include a deceleration fuel shut off (DFSO) event. In a DFSO event, only ambient air flows past the oxygen sensor and thus the sensor is exposed to a condition of lower humidity than during normal fueling conditions (e.g., such as when the engine is injecting fuel into engine cylinders). As can be observed from plot 312, lower humidity conditions may exacerbate Ip undershoots. Ip undershoot 316 under DFSO conditions is greater than the Ip undershoot 306 under normal fueling conditions. Additionally during DFSO conditions, an Ip overshoot 314 is observed when the reference voltage is stepped up from a first lower voltage to a second higher voltage. In this case, the Ip exceeds its target upper value ($I_3$) and then takes time to settle back down to the upper Ip value $I_3$. Both the Ip overshoot 314 and the lag in settling time can cause sensor degradation. Lower humidity conditions exemplified during DFSO events may result in both Ip overshoots and undershoots and can therefore lead to increased sensor damage and reduced sensor function. Thus, step changes in reference voltage of an oxygen sensor, and lower humidity conditions, can both contribute to sensor degradation.

Turning now to FIG. 4, a graph 400 shows two plots of an oxygen sensor Ip resulting from two different ramp rates used to adjust the oxygen sensor Vs between a first lower value and a second higher value. Vs alternates between first and second values in order to determine various engine operating parameters (e.g., water content of exhaust gas, water content of intake air, ambient humidity, amount of alcohol in the fuel injected into the engine, etc.) using the methods described earlier in FIG. 3. Vs plots 402 and 404 show a first lower voltage ($V_1$) being ramped up to a second higher voltage ($V_2$), but at different rates. Vs plot 402 shows the rate of increase from $V_1$ to $V_2$ and decrease from $V_2$ to $V_1$ to be less than that of Vs plot 404. Graph 400 also includes Ip plot 406 resulting from the voltage applied in Vs plot 402 and Ip plot 408 resulting from the voltage applied in Vs plot 404. In Ip plot 406, the magnitude of the Ip overshoot 412 and the magnitude of the Ip undershoot 416 are smaller than the magnitude of the Ip overshoot 410 and the magnitude of the IP undershoot 418 in plot 408. Thus, ramping up the oxygen sensor reference voltage from $V_1$ to $V_2$ at a more gradual rate, as in plot 402, as compared to the faster rate in plot 404, may decrease the magnitude of the Ip overshoot. Similarly, reducing the voltage from $V_2$ to $V_1$ at a more gradual rate as in plot 402, as compared to as the faster rate in plot 404, may decrease the magnitude of an Ip undershoot.

In one example, the rate of change in the reference voltage shown in plot 404 may be a single step change where the reference voltage transitions directly from $V_1$ to $V_2$ and back again. In another example, the rate of change in the reference voltage shown in plot 404 may be at a faster rate (and thus the plot 404 has a larger slope) than the rate of change in the reference voltage shown in plot 404 (which may have a smaller slope). Transitioning between $V_1$ and $V_2$ at a rate less than that of a single step change and/or reducing the rate of change between $V_1$ and $V_2$ may reduce the magnitude of Ip overshoots and undershoots, thereby reducing degradation of an oxygen sensor due to sensor blackening and/or pumping current ringing. As a result, the lifespan of the oxygen sensor may be increased. Further, reducing the rate of change between $V_1$ and $V_2$ may decrease settling times (e.g., decrease a time it take for the sensor to return to its base voltage $V_1$), thereby decreasing a time spent in open loop fuel operation.

Figure 5:
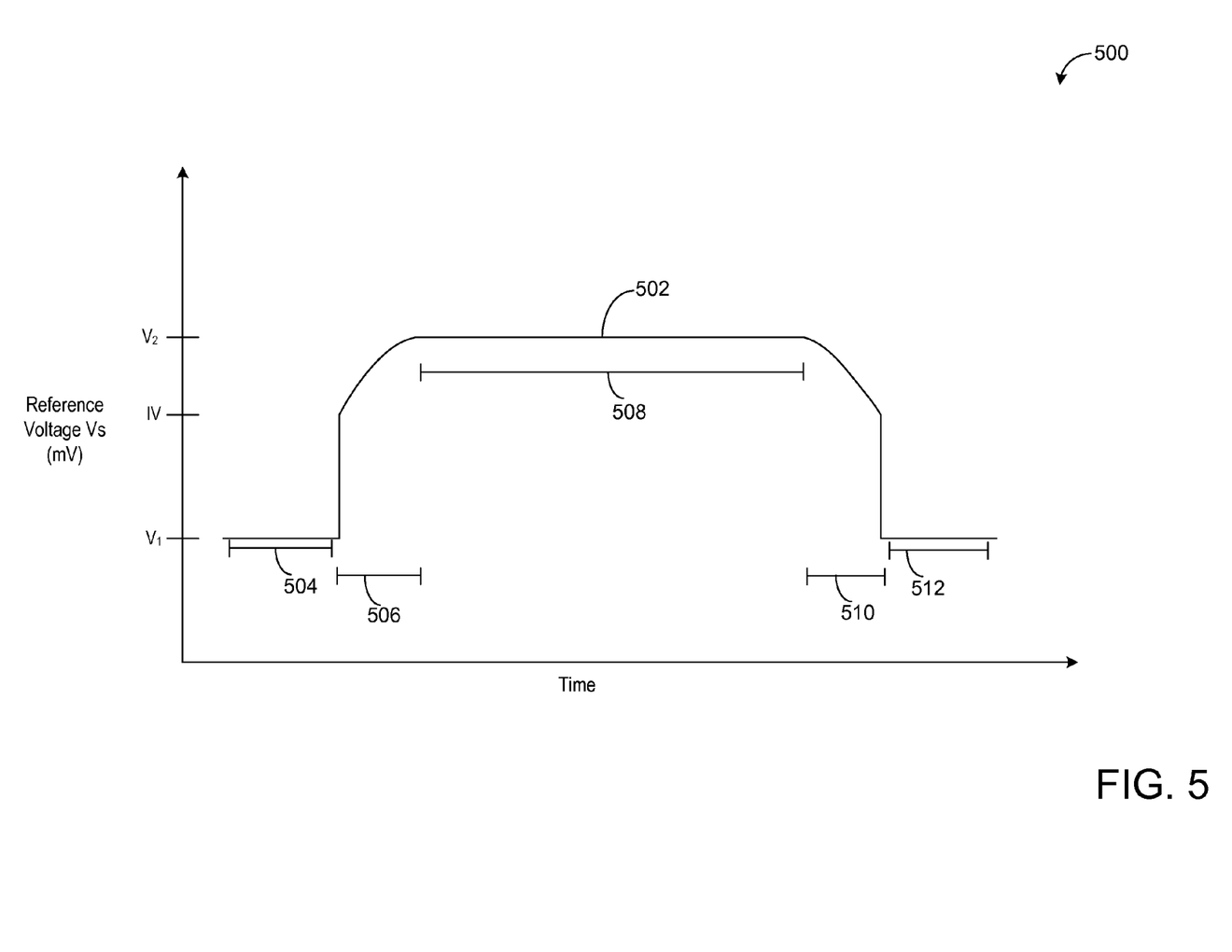
FIG. 5 shows an example waveform of a change in reference voltage of an oxygen sensor including a single step change and a slower ramped rate change.

FIG. 5 shows a graph 500 of an example ramp function for transitioning a reference voltage (Vs) of an oxygen sensor between a lower first voltage, $V_1$, and a higher second voltage, $V_2$. The purpose of the ramp function is to provide a more gradual transition between the first and second voltages so that sensor degradation may be reduced. During time interval 504, a first reference voltage (e.g., first voltage) is applied across the pumping cell (e.g. pumping electrodes pair 212 and 214) that is low enough such that water molecules are not disassociated. In one example, the first voltage is approximately 450 mV. In other embodiments, the first voltage may be a different reference voltage at which water is not dissociated. The first voltage can generate a pumping current that can be used to measure the oxygen content of the gas sample, as described in the methods of as described above.

The reference voltage is then increased from the first voltage at which water molecules are not disassociated to a second voltage at which water molecules are disassociated during time interval 506. In one example, the second voltage may be approximately 1.2 V (e.g., 1200 mV). In alternate embodiments, the second voltage may be a different voltage at which water molecules are dissociated at the sensor. Application of the second voltage during time interval 508 may generate a second pumping current that can be used to estimate the amount of oxygen and water in the sample gas which can then be used to estimate the ambient humidity and alcohol content in the injected fuel, as described in greater above. Subsequently, during time interval 510, the reference voltage is reduced from the second voltage to the first voltage and the first voltage is maintained in time interval. What will follow is a description of several embodiments of methods for increasing or decreasing the Vs between the first lower and second higher voltage. It is important to note that in all the following methods, the rates at which voltages are increased or decreased may be either pre-set or may be variable depending on the operating parameters of the vehicle engine. As an example, if lower humidity conditions are detected, the rate at which the oxygen sensor ramps between the first and second reference voltages may be reduced since lower humidity conditions may result in greater sensor degradation (as described in greater detail in FIG. 7).

During time intervals 506 and 510, the reference voltage may transition between the first and second voltages at an adjustable ramp rate. The ramp rate may be a linear function, or another smooth function whose rate of increase may gradually diminish as the reference voltage approaches the second upper voltage. In another embodiment, the voltage may be increased in a series of small incremental steps that may be the same in size or may decrease in size as the reference voltage approaches the second voltage.

In another embodiment, as depicted in plot 502 during time interval 506, the reference voltage may be increased from the first voltage $V_1$ to an intermediate voltage, IV, where water molecules just begin to become disassociated in one single step. Said another way, the reference voltage may increase directly from the first voltage to the intermediate voltage IV via a step change and without any additional intervening steps. In one example, as shown in graph 500, the intermediate voltage is approximately 900 mV. In another example, the intermediate voltage may be a different voltage between the first and second voltages where water molecules transition from not being dissociated to being dissociated at the oxygen sensor. In yet another example, the intermediate voltage may be a reference voltage before which water molecules begin to dissociate at the oxygen sensor.

The reference voltage then gradually increases from the intermediate voltage to the second voltage. Since sensor degradation may not occur when stepping between voltage levels at which water molecules do not disassociate (e.g. between 450 and 900 mV), a ramp function may not be implemented in time interval 506 to increase Vs from the first voltage to the intermediate voltage. Thus, transitioning from the first to the intermediate voltage in one step reduces a time spent at benign voltage levels and increases the rate of sampling the sensor can perform, thus increasing its precision. The reduced rate at which the reference voltage may increase from the intermediate voltage to the second voltage may be determined by a linear function, or another smooth function whose rate of increase may gradually diminish as the reference voltage approaches the second upper voltage. The voltage may also be increased from the intermediate to second voltage in a series of small incremental step that may be the same in size or may decrease in size as the reference voltage approaches the second voltage. This same process may be applied in the reverse as seen in time interval 510 of plot 502. Reference voltage may be decreased from a second voltage to an intermediate voltage at which water molecules begin to stop disassociating (e.g. 900 mV) in a gradual ramping fashion (e.g. in incremental steps, or by linear or other smooth function). Finally, the reference voltage may be reduced from the intermediate voltage to the first voltage in a single step (or at a higher rate than the ramp rate from the second voltage to the intermediate voltage).

As such, in one embodiment, methods may include ramping (or transitioning) the reference voltage of an oxygen sensor between a first and second voltage at a more gradual rate than that of a single step change. In another embodiment, methods may include reducing the rate at which the reference voltage transitions between the first and second voltages. As a result, of reducing the rate of transitioning between first and second oxygen sensor reference voltages, oxygen sensor degradation may be reduced.

Figure 6:
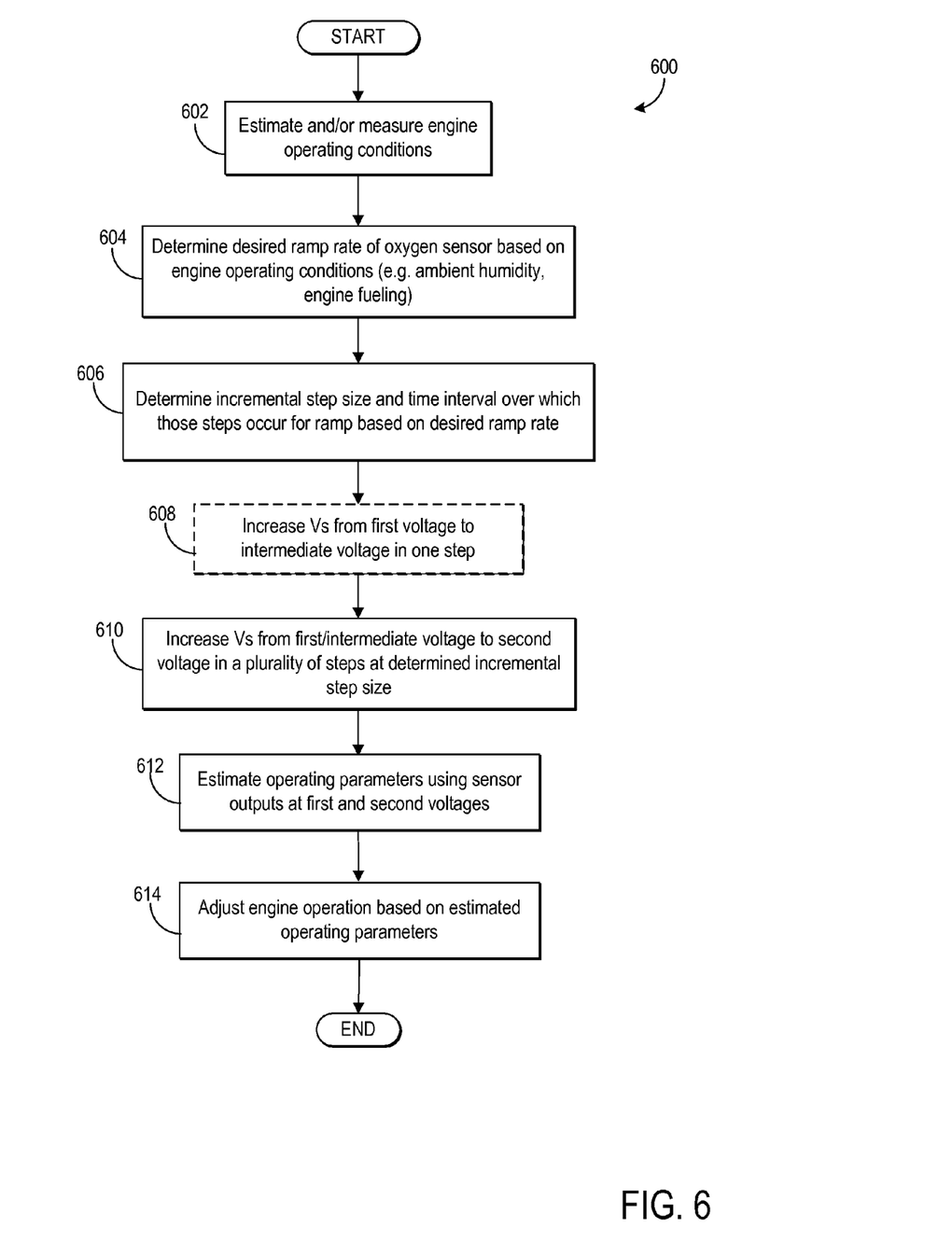
FIG. 6 shows a flow chart illustrating a method for adjusting operation of an oxygen sensor.

FIG. 6 shows a method 600 for adjusting operation of an oxygen sensor (such as oxygen sensor 126 or 127 shown in FIG. 1). Instructions for carrying out method 600 may be stored on a memory of a controller (e.g., read only memory chip 106 of controller 12 shown in FIG. 1). As such, the controller may execute method 600 based on signals received from various engine sensors, as described above at FIG. 1.

Method 600 begins at 602 by estimating and/or measuring engine operating parameters. Engine operating parameters include ambient humidity, engine speed and load, air-fuel ratio, mass air flow, engine temperatures, a fuel injection amount, etc. Method 600 proceeds from 602 to 604 where the controller determines a desired ramp rate of the oxygen sensor based on engine operating conditions. As described above, the desired ramp rate may be a desired rate at which the reference voltage of the oxygen sensor is be adjusted between a first voltage and a second voltage. The first voltage may be a lower, base voltage at which water molecules are not dissociated and the second voltage may be a higher, target voltage at which water molecules are dissociated. The desired ramp rate may be based on engine operating conditions including ambient humidity and engine fueling conditions. For example, as ambient humidity decreases, the desired ramp rate may decrease. In another example, as engine fuel decreases, the desired ramp rate may decrease. In yet another example, the desired ramp rate may be slower during non-fueling conditions, such as a deceleration fuel shut off event (DFSO), than when the engine is injecting fuel into engine cylinders. In still other examples, as the amount of oxygen in the air surrounding the oxygen sensor increases, the desired ramp rate may decrease.

At 606, the method includes determining the desired incremental step size and the time interval over which the steps occur for the ramp based on the determined desired ramp rate. The desired incremental step size may be based on the time interval over which the ramp (or increase from the first voltage to the second voltage) occurs, the desired ramp rate, and a desired step size. The desired step size may be a desired incremental increase in reference voltage. The desired step size may also be based on a number of total steps in the ramp. Alternately, the total number of steps in the ramp may be based on the ramp rate, step size, and time interval for the ramp.

Once the controller determines the incremental step size, it then sends a signal to the oxygen sensor to adjust the reference voltage accordingly. It is important to note that during each ramp, when the voltage is being increased from a first to a second voltage, the incremental step size may not be constant. As an example, it may be desirable for the rate of increase of the voltage to diminish as the applied voltage approaches the second upper voltage where greater sensor damage may occur. In another embodiment of step 606, a smooth ramping function may be implemented (e.g. linear, logarithmic or another smooth function). In this embodiment, the slope, or rate of increase of the reference voltage, is determined from step 604. The ramp rate may be constant (e.g., linear), but may also vary during the time interval that the voltage increases from the first to the second voltage. As an example, the ramp rate may decrease as the applied voltage approaches the second voltage where water disassociates and can potentially cause greater damage to the sensor.

After determining the desired ramp rate, the incremental step size (if the ramp function is not a smooth function), and the time interval for the voltage increase, method 600 may optionally proceed to 608 where the controller sends a signal to the oxygen sensor to increase the reference voltage from the first voltage to an intermediate voltage in one step (e.g., not at a reduced rate of increase). The intermediate voltage may be a voltage greater than the first voltage and less than the second voltage. In one example, the intermediate voltage may be a reference voltage at which water begins to become disassociated. In another example, the intermediate reference voltage may be a reference voltage above which water is dissociated. In yet another example, the intermediate voltage may be a reference voltage at which water is not dissociated. As such, the reference voltage of the oxygen sensor is increased via a step function from the first voltage to the intermediate voltage before initiating the decreased ramping rate determined in step 604.

Method 600 may proceed to step 610 from either step 606 or optional step 608. If method 600 arrives at step 610 from step 606, then the controller sends a signal to the oxygen sensor to adjust the reference voltage from the first to the second voltage at the rate or step size determined in steps 604 and/or 606. Alternatively, if method 600 arrives at step 610 from step 608, then the controller sends a signal to the oxygen sensor to adjust the reference voltage from the intermediate voltage to the second voltage at the rate or step size determined in steps 604 and/or 606. Thus, by incorporating step 608 into method 600, the reference voltage may be increased from a first to a second voltage in less time than by proceeding directly from step 606 to step 610, because the gradual ramping starts from a higher voltage (e.g., the intermediate voltage instead of the base first voltage) which results in a higher cycling rate for the sensor. As such, the precision of measurements of the oxygen sensor may be increased. In addition, if method 600 engages optional step 608, the health of the sensor may not be reduced because sensor degradation may only occur in voltage step intervals at which water disassociates at the sensor, as described in greater detail above with reference to FIG. 5.

Once the applied voltage reaches the desired second upper voltage at step 610, method 600 proceeds to step 612 where the controller may estimate engine operating parameters based on feedback from the sensor at the first and second voltages. The controller can determine the ambient humidity, engine air-fuel ratio, water content of the gas in the vicinity of the oxygen sensor, alcohol content in the fuel, and EGR rate, or the like based on a difference in pumping current of the oxygen sensor at the first and second voltages. Method 600 then proceeds to step 614 where the controller adjusts engine operation based on the estimated operating parameters (e.g., the operating parameters estimated based on the oxygen sensor outputs). As an example, the engine may increase the amount of exhaust gas recirculated to the intake passage if the amount of uncombusted fuel in the exhaust passage reaches a high enough first threshold. In another example, the controller may adjust fuel injection based on the estimated air-fuel ratio.

In this way, the controller may adjust engine operation based on outputs of the oxygen sensor. Further, the controller may determine the rate at which the oxygen sensor's reference voltage is increased from a first lower voltage to a second higher voltage (and decreased from the second voltage to the first voltage) based on engine operating parameters including ambient humidity and engine fueling. As a result, oxygen sensor degradation from sensor blackening and ringing may be reduced.

As shown in FIG. 6, in one embodiment, a method includes increasing a reference voltage of an oxygen sensor from a first voltage to an intermediate second voltage in a single step; and increasing the reference voltage from the intermediate second voltage to a third voltage incrementally in a plurality of steps. In one example, a step size of each of the plurality of steps is based on a desired ramp rate, a total ramp time for increasing from the intermediate second voltage to the third voltage, and a desired step time length. Further, the desired ramp rate may be based on one or more of ambient humidity and engine fueling conditions. The method may further comprise decreasing the desired ramp rate and increasing the total ramp time during a deceleration fuel shut off event. In one example, the method may further comprise decreasing the desired ramp rate and increasing the total ramp time as ambient humidity decreases. The first voltage may be a base voltage where water is not dissociated and the third voltage may be a target voltage where water is dissociated. Further still, the intermediate second voltage is between the first voltage and the third voltage.

FIG. 7 shows a graph 700 which demonstrates how the controller (e.g. controller 12 shown in FIG. 1) may adjust the reference voltage ramp rate of an oxygen sensor between a lower first voltage and a higher second voltage based on engine operating parameters such as fueling and/or ambient humidity. Plot 706 depicts how the fuel injected into the engine may change over time, and similarly plot 708 shows how the ambient humidity of air passing through the engine may change over time. Plot 702 shows adjustments to the reference voltage ramp rate of the oxygen sensor in response to the changes in fueling and/or ambient humidity from plots 706 and 708. Plot 704 shows the resulting oxygen sensor pumping current changes in plot 702.

Both fueling and ambient humidity are shown to be at a first level between times $t_0$ and $t_1$. Thus, this time interval may represent normal engine operating conditions where the engine is being fueled (e.g., fuel is being injected into engine cylinders) and ambient humidity is above a lower threshold level. At time $t_1$ the controller may detect a decrease below a threshold level in the amount of fuel being injected into the engine. In one example, the decrease in engine fueling below the threshold level may be the result of a DFSO event or other non-fueling condition. This may decrease the humidity of the gas mixture since water from the fuel contributes to the overall humidity of the gas mixture in the combustion chamber. Additionally, during the non-fueling conditions, the oxygen content in the exhaust gas flowing to an exhaust oxygen sensor (positioned in an exhaust passage downstream of engine cylinders) may increase. This decrease in humidity and increase in oxygen content may result in increased pumping current overshoots, undershoots, and/or settling times of the oxygen sensor, thereby contributing to degradation of the sensor. Thus, in response to the decrease in engine fueling, the controller may decrease the ramp rate at which the reference voltage of the oxygen sensor (e.g., the exhaust oxygen sensor) increases from a first voltage to a second voltage and decrease from the second voltage to the first voltage. This can be observed in plot 702. Between times $t_1$ and $t_2$, where the fuel injected to the engine decreases from the first level F1, the rate at which the reference voltage increases from the first lower voltage to the second higher voltage (e.g., second slope 712 of the line of plot 702), is less than the rate between times $t_0$ and $t_1$ (e.g., less than first slope 710 of the line of plot 702).

Once fueling conditions return to the first level F1 at time $t_2$, the ramp rate (e.g., the rate of change between the first and second voltages) of the reference voltage in plot 702 is returned to a similar rate of that during the time interval from $t_0$ to $t_1$. Thus, the ramp rate of the reference voltage is increased again after time $t_2$. At time $t_3$, the controller detects a decrease below a lower threshold level in the ambient humidity from the first level A1. This may happen when the vehicle enters a particularly dry environment, where the moisture content in the ambient air is very low. Since low humidity conditions may result in increased oxygen sensor degradation, the controller may reduce the ramp rate at which the reference voltage transitions between the lower first voltage and the higher second voltage. As seen in plot 702 after time $t_3$, the rate of change between the lower first voltage and the higher second voltage (e.g., the third slope 714 of the line in plot 702) is less than that between times $t_0$ and $t_1$ and $t_2$ and $t_3$ when and the ambient humidity is at the first level A1 and engine fueling is at the first level F1.

As observed in plot 702, the ramp rate of the voltage increase or decrease between the lower first voltage and the higher second voltage may be adjusted based on engine operating conditions. The ramp rate (also referred to herein as the rate of change of the reference voltage) may decrease as the amount of fuel being injected into cylinders of the engine and/or the ambient humidity decreases. In another example, the ramp rate may only decrease when the fuel injection amount and/or the ambient humidity decrease below respective threshold levels, the threshold levels based on levels at which oxygen sensor overshoots, undershoots, and/or settling times in the pumping current output may result in sensor degradation. In some examples, a DFSO event may coincide with lower humidity conditions. In this example, the ramp rate of the oxygen sensor reference voltage may decrease responsive to both the DFSO and decreased humidity conditions. For example, the ramp rate may be decreased to a greater extent (the transition between the first voltage and the second voltage may be even more gradual) than observed between times $t_1$ and $t_2$ or after $t_3$ if the controller detects both a lower humidity condition and a DFSO event. That is to say that a DFSO event (or non-fueling event) and decreased humidity event may not be exclusive, and both occurring simultaneously may result in a more gradual ramp rate than observed in graph 700.

The ramp rate, or the more gradual transition between the first voltage (e.g., base voltage at which water is not dissociated) and the second voltage (e.g., target voltage at which water is dissociated), is less than the rate of a single step (also referred to as a single step change between the first and second voltages). As described herein, during engine operation, the oxygen sensor reference voltage alternates between the lower first voltage and the higher second voltage over a time interval at a rate set by the controller based on engine operating conditions. The rate of change between reference voltages may then be adjustable based on the engine operating parameters. However, in one embodiment, the rate of change in reference voltage (e.g., ramp rate) may always be less than the rate of change of a single direct step change between the first and second voltages. Thus, there may be a threshold ramp rate, based on the rate of a single step change between voltages, that the oxygen sensor ramp rate may remain below.

In this way, a method may include gradually changing a reference voltage of an oxygen sensor between a first voltage and a second voltage at a ramp rate, the ramp rate based on engine operating conditions. As described above, the oxygen sensor may be a variable voltage oxygen sensor positioned in an exhaust or intake passage of an engine. The reference voltage of the variable voltage oxygen sensor is adjustable between the first voltage and the second voltage, where the first voltage is a lower voltage at which water is not dissociated at the sensor and the second voltage is a higher voltage at which water is dissociated at the sensor. A technical effect is achieved by gradually adjusting the oxygen sensor reference voltage at a ramp rate based on engine operating conditions, thereby decreasing oxygen sensor degradation and increasing an accuracy of engine control based on oxygen sensor outputs. Specifically, transitioning between the first and second voltages at a slower ramp rate may decrease sensor overshoots, undershoots, and settling times that may result in sensor ringing and blackening effects that may degrade the sensor. Further, as the oxygen content in the gas surrounding the oxygen sensor increases, these effects may become more pronounced. Thus, further decreasing the reference voltage ramp rate of the oxygen sensor as the oxygen content of the exhaust and/or intake gas increases (e.g., such as during decreased engine fueling for an exhaust oxygen sensor and decreased ambient humidity for both intake and exhaust oxygen sensors), may further reduce degradation of the oxygen sensor.

As one embodiment, a method includes increasing a reference voltage of an oxygen sensor from a first voltage to a second voltage gradually at a ramp rate, the ramp rate based on engine operating conditions. In one example, the ramp rate is based on ambient humidity with the ramp rate decreasing with decreasing ambient humidity. In one example, the ramp rate is based on engine fueling with the ramp rate decreasing with decreasing engine fueling. The method further includes decreasing the ramp rate from a first level to a lower second level during an engine non-fueling condition.

In one embodiment, the method further comprises increasing the reference voltage from the first voltage to an intermediate voltage with a single step change and then increasing the reference voltage from the intermediate voltage to the second voltage at the ramp rate, a rate of change of the ramp rate smaller than the single step change. In one example, the intermediate voltage is a voltage below which water is not dissociated and above which water is dissociated. Additionally, the first voltage is a base reference voltage and the second voltage is a target voltage at which water is dissociated. The method further includes decreasing the reference voltage from the second voltage to the first voltage gradually at the ramp rate. In one example, the oxygen sensor is an exhaust oxygen sensor positioned in an exhaust passage of an engine and the method further includes determining a water content of exhaust air based on outputs of the oxygen sensor at the first voltage and the second voltage. The method may further include estimating a fuel alcohol content based on the determined water content. In another example, the oxygen sensor is an intake oxygen sensor positioned in an intake manifold of an engine and the method further includes determining a water content of intake air based on outputs of the oxygen sensor at the first voltage and the second voltage.

In yet another embodiment, an engine system may include an exhaust oxygen sensor positioned in an exhaust passage downstream of an engine cylinder and a controller with computer readable instructions for: during a first condition when the engine cylinder is being fueled, increasing a reference voltage of the exhaust oxygen sensor from a first voltage to a second voltage gradually at a first ramp rate and during a second condition when the engine cylinder is not being fueled, increasing the reference voltage of the exhaust oxygen sensor from the first voltage to the second voltage gradually at a second ramp rate, the second ramp rate more gradual than the first ramp rate. Increasing the reference voltage of the exhaust oxygen sensor from the first voltage to the second voltage during the first and second conditions includes increasing the reference voltage from the first voltage to the second voltage in a series of incremental steps, a number of incremental steps and size of each of the series of incremental steps based on each of the first ramp rate and the second ramp rate. Further, the exhaust oxygen sensor is a variable voltage oxygen sensor, where the first voltage is a base voltage, and where the second voltage is a target voltage, the target voltage based on a desired gas constituent to be measured by the exhaust oxygen sensor. The engine system may further include an intake oxygen sensor located in an intake passage upstream of the engine cylinder.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for adjusting operation of an oxygen sensor of an engine, comprising:
during a first increase in reference voltage of the oxygen sensor from a first voltage to a second voltage, gradually increasing the reference voltage applied to the oxygen sensor at a first rate of increase in the reference voltage; and
during a second increase in reference voltage of the oxygen sensor from the first voltage to the second voltage, responsive to a change in an engine operating condition, gradually increasing the reference voltage applied to the oxygen sensor at a second rate, where the oxygen sensor is a variable voltage oxygen sensor having the reference voltage that is adjustable.

2. The method of claim 1, wherein the change in the engine operating condition includes a change in ambient humidity, wherein the second rate decreases relative to the first rate in response to decreasing ambient humidity, and wherein the reference voltage of the variable voltage oxygen sensor is adjustable responsive to a signal sent to the oxygen sensor via a controller of the engine.

3. The method of claim 1, wherein the change in the engine operating condition includes a change in engine fueling and wherein the second rate decreases relative to the first rate in response to decreasing engine fueling.

4. The method of claim 3, wherein the engine operating condition includes an engine non-fueling condition and wherein the second rate is lower than the first rate.

5. The method of claim 1, further comprising, during both the first increase in reference voltage and the second increase in reference voltage, increasing the reference voltage from the first voltage to an intermediate voltage, the intermediate voltage between the first voltage and the second voltage, with a single step change, and then increasing the reference voltage from the intermediate voltage to the second voltage gradually at the first or second rate, a rate of change of the first and second rates smaller than the single step change.

6. The method of claim 5, wherein the intermediate voltage is a voltage that is above a voltage at which water is not dissociated and below a voltage at which water is dissociated.

7. The method of claim 1, wherein the first voltage is a base reference voltage and the second voltage is a target voltage at which water is dissociated, wherein the first voltage and the second voltage are each greater than zero, and wherein the gradually increasing the reference voltage includes gradually increasing the reference voltage applied to an oxygen pumping cell of the oxygen sensor.

8. The method of claim 1, further comprising, during a first decrease in the reference voltage from the second voltage to the first voltage, following the first increase, decreasing the reference voltage from the second voltage to the first voltage gradually at the first rate and during a second decrease in the reference voltage from the second voltage to the first voltage, following the second increase, decreasing the reference voltage from the second voltage to the first voltage at the second rate, and wherein the first rate and the second rate are rates of change in the reference voltage of the oxygen sensor between the first voltage and the second voltage.

9. The method of claim 1, wherein the oxygen sensor is an exhaust oxygen sensor positioned in an exhaust passage of the engine and further comprising determining a water content of exhaust air based on a difference in pumping current output by the oxygen sensor at the first voltage and the second voltage.

10. The method of claim 9, further comprising estimating a fuel alcohol content based on the determined water content.

11. The method of claim 1, wherein the oxygen sensor is an intake oxygen sensor positioned in an intake manifold of the engine and further comprising determining a water content of intake air based on a difference in pumping current output by the oxygen sensor at the first voltage and the second voltage.

12. A method for an engine including an oxygen sensor, comprising:
during repeatedly transitioning a reference voltage of the oxygen sensor, where the oxygen sensor is a variable voltage oxygen sensor having the reference voltage that is adjustable, between a first voltage and a third voltage, for a first increase in the reference voltage from the first voltage to the third voltage,
first increasing the reference voltage applied to the oxygen sensor from the first voltage to an intermediate second voltage in only a single step; and
then increasing the reference voltage applied to the oxygen sensor from the intermediate second voltage to the third voltage incrementally in a plurality of steps; and
adjusting engine operation based on an engine operating parameter estimated based on a difference in pumping current output by the oxygen sensor at the first voltage and the third voltage.

13. The method of claim 12, wherein a step size of each of the plurality of steps is based on a desired ramp rate, a total ramp time for increasing from the intermediate second voltage to the third voltage, and a desired step time length.

14. The method of claim 13, wherein the desired ramp rate is based on one or more of ambient humidity and engine fueling conditions.

15. The method of claim 14, further comprising, during a second increase in the reference voltage from the first voltage to the third voltage that occurs during a deceleration fuel shut off event, decreasing the desired ramp rate and increasing the total ramp time.

16. The method of claim 14, further comprising, during a second increase in the reference voltage from the first voltage to the third voltage and in response to a decrease in ambient humidity, decreasing the desired ramp rate and increasing the total ramp time.

17. The method of claim 12, wherein the first voltage is a base voltage where water is not dissociated and the third voltage is a target voltage where water is dissociated and wherein the intermediate second voltage is between the first voltage and the third voltage.

18. An engine system, comprising:
an exhaust oxygen sensor positioned in an exhaust passage downstream of an engine cylinder, where the exhaust oxygen sensor is a variable voltage oxygen sensor having a reference voltage that is adjustable; and
a controller with computer readable instructions for:
during a first condition when the engine cylinder is being fueled, increasing the reference voltage of the exhaust oxygen sensor from a first voltage to a second voltage gradually at a first ramp rate of increase in the reference voltage; and during a second condition when the engine cylinder is not being fueled, increasing the reference voltage of the exhaust oxygen sensor from the first voltage to the second voltage gradually at a second ramp rate of increase in the reference voltage, the second ramp rate more gradual than the first ramp rate.

19. The system of claim 18, wherein increasing the reference voltage of the exhaust oxygen sensor from the first voltage to the second voltage during the first and second conditions includes increasing the reference voltage from the first voltage to the second voltage in a series of incremental steps, a number of incremental steps and a size of each of the series of incremental steps based on each of the first ramp rate of increase in the reference voltage and the second ramp rate of increase in the reference voltage.

20. The system of claim 18, wherein the first voltage is a base voltage, and wherein the second voltage is a target voltage, the target voltage based on a desired gas constituent to be measured by the exhaust oxygen sensor.

* * * * *